United States Patent
Kramer et al.

(10) Patent No.: US 12,171,730 B2
(45) Date of Patent: Dec. 24, 2024

(54) HEXYLAMINE SALTS AND METHODS OF USING HEXYLAMINE

(71) Applicant: ThermoLife International, LLC, Signal Hill, CA (US)

(72) Inventors: Ronald Kramer, Signal Hills, CA (US); Alexandros Nikolaidis, Nea Kallikratia (GR)

(73) Assignee: ThermoLife International, LLC, Signal Hill, CA (US)

( * ) Notice: Subject to any disclaimer, the term of this patent is extended or adjusted under 35 U.S.C. 154(b) by 163 days.

(21) Appl. No.: 18/092,800

(22) Filed: Jan. 3, 2023

(65) Prior Publication Data

US 2023/0149325 A1     May 18, 2023

Related U.S. Application Data

(62) Division of application No. 16/850,942, filed on Apr. 16, 2020, now Pat. No. 11,541,020.

(60) Provisional application No. 62/834,878, filed on Apr. 16, 2019.

(51) Int. Cl.
| | |
|---|---|
| *A61K 31/131* | (2006.01) |
| *A23L 33/10* | (2016.01) |
| *A61K 9/00* | (2006.01) |
| *A61K 31/194* | (2006.01) |
| *A61K 31/522* | (2006.01) |
| *A61K 45/06* | (2006.01) |

(52) U.S. Cl.
CPC ............ *A61K 31/131* (2013.01); *A23L 33/10* (2016.08); *A61K 31/194* (2013.01); *A61K 9/0053* (2013.01); *A61K 31/522* (2013.01); *A61K 45/06* (2013.01)

(58) Field of Classification Search
CPC .... A61K 45/06; A61K 31/131; A61K 31/194; A23L 33/10
See application file for complete search history.

(56) References Cited

U.S. PATENT DOCUMENTS

| | | |
|---|---|---|
| 2,398,706 A | 4/1946 | Haas |
| 2,811,429 A | 10/1957 | Lappin |

OTHER PUBLICATIONS

E Widy-Tyszkiewicz, A Członkowski, "Effect of Aliphatic Monoamines on Motor Activity of Mice: No Direct Interaction With Dopaminergic D2 Receptor", Polish journal of pharmacology and pharmacy, PL, (Nov. 30, 1982), vol. 35, No. 6, ISSN 0301-0244, pp. 467-472, XP009530727.
Hitoshi Aoshima et al. «Modulation of GABA Receptors Expressed in Xenopus Oocytes by 13-I-Hydoxylinoleic Acid and Food Additives» Bioscience, Biotechnology, and Biochemistry, 61, 12, 1997,2051-2057, abstract.
Kazushi Nomura et al. «Aminoglycoside Blockade of Ca2+-Activated K + Channel torn Rat Brain Synaptosomal Membranes Incorporated into Planar Bilayers» J. Membrane Biol. 115,241-251, 1990, chapter Chemicals p. 242, fig. 8.
Ktenas, Theodore B., et al. «Interaction of Aliphatic Amines with Glycogen Phosphorylase» J. Biochem. 92,2029-2033, 1982, abstract, tables 1, 2.
NoorAzuinSuliman et al «Establishing Natural Nootropics: Recent Molecular Enhancement Influenced by Natural Nootropic» Evidence-Based Complementary and Alternative Medicine vol. 2016, Article ID 4391375,12 pages http://dx.doi.Org/10.1155/2016/4391375, abstract.
Novel strategies for online detection of doping compounds in breath using secondary electrospray ionization mass spectrometry dissertation for the degree of Doctor of Sciences Meier, Lukas Christian, 2012,1-142, fig.3.2.
Pfundstein etal., "Mean Daily Intake of Primary and Secondary Amines From Food and Beverages in West Germany in 1989-1990", Food and Chemical Toxicology, vol. 29, No. 11, pp. 733-739 (1991).
Ralston, A. W. «The Preparation and Properties of High Molecular Weight primary Amines», Oil & Soap, Apr. 1940, 89-91, p. 91 left column paragraphs 1,2.
Valeria Catalani et al «Octodrine: New Questions and Challenges in Sport Supplements» Brain Sci. 2018, 8, 34, 1-13, abstract.

*Primary Examiner* — Kevin E Weddington
(74) *Attorney, Agent, or Firm* — Booth Udall Fuller, PLC; Pacer K. Udall

(57) ABSTRACT

Salts of hexylamine, for example, hexylamine succinate and tri-hexylamine citrate and their method of production are described. The disclosure also relates to compositions comprising hexylamine, for example, for reducing appetite in a human subject, treating obesity in a human subject, preventing obesity in a human subject, preventing weight gain in a human subject, increasing fat loss in a human subject, treating an overweight human subject, increasing athletic performance in a human subject, increasing endurance in a human subject, increasing muscle strength in a human subject, improving cognitive function in a human subject, treating ADHD in a human subject, increasing sweating in a human subject, reducing reaction time of a human subject, increasing psychomotor vigilance of a human subject, enhancing memory in a human subject, increasing central nervous system activity in a human subject, and enhancing alertness, attention, concentration, and/or memory in a human subject.

6 Claims, 2 Drawing Sheets

HEXYLAMINE SALTS AND METHODS OF USING HEXYLAMINE

CROSS REFERENCE TO RELATED APPLICATIONS

The present application is a division of U.S. utility patent application Ser. No. 16/850,942, filed Apr. 16, 2020, which application claims the benefit of and priority to U.S. provisional patent application 62/834,878, filed Apr. 16, 2019, the entirety of the disclosures of which are hereby incorporated by this reference.

BACKGROUND

Hexylamine, also known as n-hexylamine, n-hexyl-ammonium, and 1-aminohexane, is a chemical compound with molecular formula $CH_3(CH_2)_5NH_2$ and the structure of Formula (I).

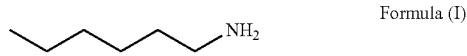

Formula (I)

Hexylamine is a colorless liquid and is one of the isomeric amines of hexane. At standard temperature and pressure, hexylamine is soluble in almost all organic solvents. It has the ammonia/bleach odor common to amines, which has also been reported as smelling "fishy." It is found in trace amounts (less than 1 ppm) in some foods, such as beer, wine, camembert cheese, and milk (Maga et al., *Amines in foods*). However, it is not known whether a human would benefit from hexylamine supplementation. When hexylamine was administered to a human, no change in blood pressure or any other physiological effect was observed (Alles, *Comparative physiological actions of aliphatic primary carbon-ammonium salts*, 1941). More than half a century after these experiments, hexylamine was labeled as being "highly toxic in any quantity" in the second edition of Phytochemical Dictionary: A Handbook of Bioactive Compounds from Plants.

SUMMARY OF THE INVENTION

In some aspects, the disclosure relates to salts of hexylamine, for example, hexylamine succinate and tri-hexylamine citrate and their method of production. The method of producing hexylamine succinate comprises gradually mixing hexylamine into succinic acid to produce a solution comprising hexylamine succinate. The temperature of the solution comprising hexylamine succinate is at a temperature lower than 131° C. The method of producing tri-hexylamine citrate comprises combining a hexylamine and citric acid at a molar ratio of 3 mol hexylamine to 1 mol citric acid. Citric acid is first dissolved in a suitable solvent to produce a saturated solution of citric acid. The suitable solvent does not chemically react to citric acid or hexylamine. Hexylamine is then added drop by drop to the saturated solution of citric acid to produce a mixture containing a precipitate. In some aspects, the saturated solution of citric acid is continually stirred during the addition of hexylamine. In some method of producing tri-hexylamine citrate, the method further comprises stirring the mixture containing the precipitate for at least 15 minutes after all of the hexylamine is added to the saturated solution of citric acid. Afterwards, the precipitate is filtered out of the mixture and dried to collect the tri-hexylamine citrate. In some aspects, the solvent for producing the saturated solution of citric acid is acetone. Accordingly, the saturated solution of citric acid is preferably prepared at a temperature of no higher than 70° C., for example at room temperature. In some implementations, the method of producing tri-hexylamine citrate further comprises filtering out the precipitate from the mixture and drying the precipitate to collect tri-hexylamine citrate.

The disclosure also relates to compositions comprising a salt of hexylamine and a dietary ingredient, a food additive or a pharmaceutically acceptable additive. In some aspects, the salt of hexylamine is selected from the group consisting of: the hydrochloride, the nitrate, the sulfate, the citrate, the malate, the maleate, the succinate, the fumarate, and the acetate. In preferred embodiments, the salt of hexylamine in the composition is hexylamine succinate or even more preferably tri-hexylamine citrate.

In other aspects, the disclosure relates methods of reducing appetite in a human subject, treating obesity in a human subject, preventing obesity in a human subject, preventing weight gain in a human subject, increasing fat loss in a human subject, treating an overweight human subject, increasing athletic performance in a human subject, increasing endurance in a human subject, increasing muscle strength in a human subject, improving cognitive function in a human subject, treating ADHD in a human subject, increasing sweating in a human subject, reducing reaction time of a human subject, and increasing psychomotor vigilance of a human subject. The methods comprise administering to the human subject a pharmaceutically effective amount of hexylamine or a suitable salt. In some implementations, the pharmaceutically effective dose provides between 5 mg and 5000 mg hexylamine, for example, between 100 mg and 800 mg hexylamine. In some aspects, the pharmaceutically effective dose is administered to the human subject two times a day. In other aspects, the pharmaceutically effective dose is administered to the human subject three times a day. In certain implementations, the human subject is administered hexylamine succinate or tri-hexylamine citrate.

DETAILED DESCRIPTION OF THE INVENTION

Figure 1:
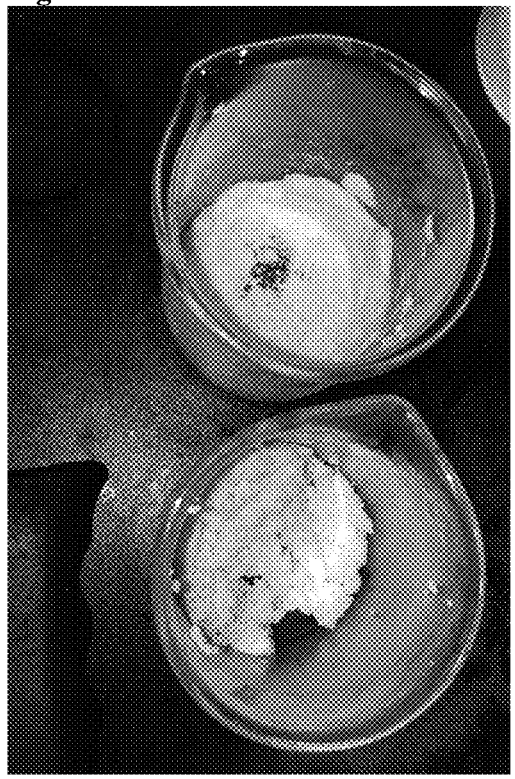
FIG. 1 depicts a comparison of hexylamine succinate and hexylamine tartrate after being left exposed to air for a period of a month. Hexylamine succinate (top beaker) remained a fine powder and gained little moisture, while hexylamine tartrate (bottom beaker) absorbed moisture from the atmosphere and suffered from extensive caking.
Figure 2:
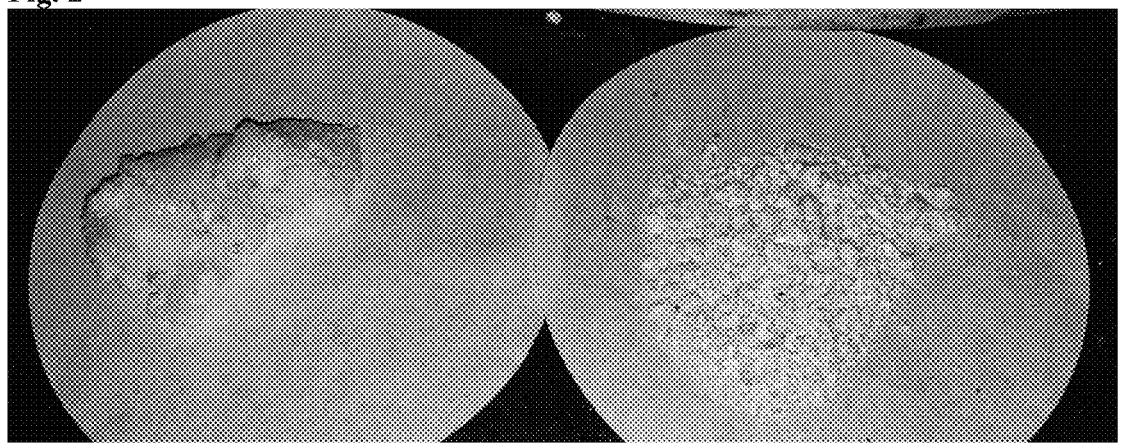
FIG. 2 depicts a comparison of monohexylamine citrate and tri-hexylamine citrate after being left exposure to air for one day. Monohexylamine citrate (left) hardened into a solid mass while tri-hexylamine citrate (right) suffered from some caking.
Figure 3:
FIG. 3 depicts a time course of tri-hexylamine citrate in water. One gram of tri-hexylamine citrate was scattered over 100 ml water at room temperature (left). About one minute after, all of the tri-hexylamine citrate was dissolved (right).

Detailed aspects and applications of the invention are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. It should be noted that there are many different and alternative configurations, devices and technologies to which the disclosed inventions may be applied. The full scope of the inventions is not limited to the examples that are described below.

The singular forms "a," "an," and "the" include plural referents unless the context clearly dictates otherwise. Thus, for example, reference to "a step" includes reference to one or more of such steps.

As used herein, the term "about" when used in the context of numeric values denotes an interval of accuracy, familiar and acceptable to a person skilled in the art. The interval can be +/−2% of the given value, preferably +/−5%, and most preferably +/−10% of the numeric values, where applicable.

As used herein, the term "room temperature" refers to a temperature range of 20 to 25° C. with excursions between 15 to 30° C., provided that the mean kinetic temperature does not exceed 25° C. In some aspects, "room temperature" refers to a temperature range of 15 to 25° C.

As used herein, the term "saturated solution" refers to a solution in which the maximum amount of solute has been dissolved. Accordingly, a saturated solution of citric acid is a solution in which the maximum amount of citric acid is dissolved in a solvent.

As used herein, the term "cognitive function" encompasses all aspects of conscious brain function. As such, cognitive function includes learning and memory, planning, attention, problem-solving, and sensory perception.

As used herein, the term "dietary supplement" refers to an addition to the human diet, which is not a natural or conventional food.

As used herein, the term "effective amount" refers to an amount that is effective for a specific patient. In some aspects, the term "effective amount" refers to a pharmaceutically effective amount, which an amount that is effective in a clinical trial.

As used herein, the term "suitable for human consumption" refers to a compound or composition that is generally safe, non-toxic, and can be used as in medication, dietary supplement or even food.

As used herein, when doses of hexylamine are referenced, the amount refers to the amount of the free base that can yield from the salt after dissociation. For example, hexylamine succinate is 219.183 Dalton, of which 46.14% is hexylamine. For tri-hexylamine citrate (495.694 Dalton), the theoretical percentage of hexylamine in the salt would be about 61%.

Hexylamine by itself is a foul-smelling liquid at room temperature. It is caustic on contact with the skin or tongue, which could explain why no one sought to increase intake of hexylamine by ingestion of the compound. To develop a salt of hexylamine that has favorable organoleptic, pharmacokinetic, and pharmacotechnical properties for use in a dietary supplement or composition for human ingestion, a variety of hexylamine salts, including the hydrochloride, the nitrate, the sulfate, the citrate, the malate, the maleate, the succinate, the fumarate, and the acetate, were synthesized. The acetate, hydrochloride, and the nitrate of hexylamine were liquid at standard temperature and pressure, which makes it unsuitable for most formulatory purposes. The fumarate of hexylamine still had an offending smell, which could be from release of hexylamine. Some of the salts synthesized showed slow dissolution rate in water, which would reduce their bioavailability. Of the other salts synthesized, hexylamine succinate and tri-hexylamine citrate were the best candidates for use in a dietary supplement or composition for human ingestion.

The succinate was the easiest to produce. In some aspects, the disclosure relates to the synthesis of hexylamine succinate. The method of producing hexylamine succinate required only direct addition of hexylamine to succinic acid at equimolar parts without the need for any additional solvents. In a preferred implementation, hexylamine is gradually mixed into succinic acid to produce a solution comprising hexylamine succinate so that the temperature of the solution comprising hexylamine succinate does not exceed 131° C. Most preferably, the solution comprising hexylamine succinate is maintained at a temperature of less than 70° C.

The resultant succinate salt can be immediately formed into powder, unlike the sulfate or fumarate salts, which require grinding in order to produce a fine powder. As the grinding process results in releasing the salt into the atmosphere, grinding hexylamine salts could results in serious health toxicity and undesired environmental modifications (for example, unpleasant odor). Unlike other salts, the succinate lacked any offending smell. The succinate also tasted the best out of the salts synthesized. And importantly, the succinate salt is non-hydroscopic. Therefore, the novel salt hexylamine succinate is a preferred choice with the unexpected properties of improved taste, good solubility and dissolution rate, improved stability, reduced hygroscopicity, ease of formulation and excellent powdered characteristics.

While similar direct combination of citric acid and hexylamine forms mono-hexylamine citrate, the salt is very hygroscopic, dense and is paste-like at room temperature. Thus, mono-hexylamine citrate is not as suitable for formulatory purposes as hexylamine succinate. However, tri-hexylamine citrate is can be milled to a powder at room temperature and is more water soluble and dissolvable than mono-hexylamine citrate. In fact, tri-hexylamine citrate dissolves faster than all other salts of hexylamine in water and has a faster effect on human subjects upon taking it as a capsule. Furthermore, low density of tri-hexylamine citrate, as shown by the powdered compound floating on might explain its higher activity compared to the mono-hexylamine citrate. Tri-hexylamine citrate is a very stable salt with the additional benefit of carrying a lot of hexylamine by weight compared to other monohexylamine salts.

To efficiently produce tri-hexylamine citrate, hexylamine is slowly added to a saturated solution of citric acid in a ratio of about 3 mol hexylamine to about 1 mol citric acid. In preferred implementations, the hexylamine is added drop by drop into the saturated solution of citric acid. During the addition of the hexylamine, the saturated solution of citric acid is continuously stirred. Once all of the hexylamine has been added to the saturated solution of citric acid, the mixture is stirred for at least another 15 minutes. The white precipitated formed in the mixture is then filtered out and dried to collect the produced tri-hexylamine citrate.

The solvent for making the solution of citric acid must be one in which citric acid and hexylamine are soluble with no chemical reactions taking place. Preferably, the solvent is not aqueous. In preferable implementations, the solvent is anhydrous. In particular implementations, the solvent is acetone to make a saturated solution of citric acid in acetone. At room temperature, the saturated solution of citric acid in acetone is prepared by adding 20 g citric acid to 1000 ml acetone. The amount of citric acid dissolvable in acetone is higher at higher temperatures. However, acetone evaporates at around 80° C. and is a fire and health hazard, so the preparation of the saturated solution of citric acid in acetone should not use acetone heated to a temperature higher than 70° C., preferably no higher than 40° C., for example, at room temperature.

While no one has studied whether ingestion of hexylamine at an amount greater than the trace amount found in food would provide any benefit to a human subject, studies have found that its chemical relatives do cause a physiological change when ingested. Propylamine, $CH_3(CH_2)_3NH_2$, a close chemical entity to hexylamine, has been used in the distant past as a sedative at doses of 2-10 grams (Page 892 of *The Standard Medical Directory of North America* 1902, GP Engelhard and Company, Chicago). Amylamine, the closest chemical entity to propylamine, has also been described as a compound that can reduce cardiac function, reduce heartbeat, and reduce body temperature, which are characteristics of a compound with a probable anti-stimulatory effect (Page 1999 of *King's American Dispensatory* (Felter and Lloyd eds., 1909), The Ohio Valley Company, Cincinnati). These early observations about amylamine were confirmed: administration of doses starting at 300 mg would among other effects produce reduction in heart rate and a drop in body temperature. Accordingly, compound having similar structure to hexylamine were expected to reduce alertness and cognitive function due to their sedative effects (from de facto slowdown of brain activity).

However, it was surprisingly discovered that administration of hexylamine to humans produced effects that were opposite those of amylamine. As shown in Example 4, the administration of hexylamine increased body temperature, heart rate, systolic blood pressure, and diastolic blood pressure. The subjects also reported increased sweating. In addition, the subjects reported experiencing positive psychological and mental changes, for example, reduced appetite, increased mental acuity, and increased memory recollection. Example 6 further demonstrates administration of hexylamine improves cognitive function, though no significant changes in heart rate, systolic blood pressure, and diastolic blood pressure were observed in the larger study. As shown in Example 4 and Example 7, administration of hexylamine caused physical performance changes, for example, reduction of fatigue, increase in athletic performance, increase in endurance, and increase in strength.

Thus, the disclosure relates to the use of hexylamine for reducing appetite in a human subject, treating obesity in a human subject, preventing obesity in a human subject, preventing weight gain in a human subject, increasing fat loss in a human subject, treating an overweight human subject, increasing athletic performance in a human subject, increasing endurance in a human subject, increasing muscle strength in a human subject, improving cognitive function in a human subject, treating ADHD in a human subject, increasing sweating in a human subject, reducing reaction time of a human subject, increasing psychomotor vigilance of a human subject, enhancing memory in a human subject, increasing central nervous system activity in a human subject, and enhancing alertness, attention, concentration, and/or memory in a human subject. The methods comprise administering to a human subject in need thereof a pharmaceutically effective amount of hexylamine or a salt thereof. The pharmaceutically effective amount of hexylamine is between about 5 mg and about 5000 mg per day, which can be taken in multiple doses during the day. In some aspects, the pharmaceutically effective amount of hexylamine in a single dose is between 50 mg and 1000 mg, between 75 mg and 750 mg, or between 100 mg and 750 mg. In particular implementations, a pharmaceutically effective amount of hexylamine in a single dose is between about 100 mg and about 600 mg.

Accordingly, the disclosure also relates to compositions comprising hexylamine or a salt thereof. For example, the disclosure relates to a stimulatory composition, a nootropic composition for boosting cognitive function, a pre-workout composition, or a composition for aiding fat loss, the compositions comprising an effective amount of hexylamine or a salt thereof. In some aspects, the effective amount of hexylamine is between about 5 mg and about 5000 mg per day, for example, between 50 mg and 1000 mg, between 75 mg and 750 mg, between 100 mg and 750 mg, about 100 mg, about 250 mg, about 500 mg, about 600 mg, or about 750 mg. the compositions are topical or suitable for human ingestion. In some aspects, the compositions further comprises one or more additional ingredient, for example, flavoring agents, colorants, viscosity modifiers, viscosity improvers, preservatives, fragrances, flow modifiers, chelating agents, surfactants (including anionic, cationic or non-ionic surfactants), amino acids (including their derivatives or salts thereof), vitamins, minerals, essential fatty acids, enzymes, co-enzymes, mono-glycerides, di-glycerides, tri-glyceride ester oils emulsifiers, hydrolyzed proteins, whey protein, stabilizers, anti-oxidants, anti-microbials, benzoates, alcohols, esters of para-hydroxybenzoic acid, propionates, herbal extracts or constituents thereof, fruit extracts or constituents thereof, vegetable extracts or constituents thereof, herbal oils, herbal infusions, herb powder, fruit powder, vegetable powder, tea extracts or constituent thereof, and/or elemental metals (for example, elemental zinc). In certain embodiments, the one or more additional ingredient in the composition is suitable for human consumption or are pharmaceutically acceptable.

In one aspects, the stimulatory composition comprises an effective amount of hexylamine or a salt thereof and an effective amount of a stimulant selected from the group consisting of: yohimbine, ephedrine, ephedra sinica extracts, 1,3-dimethylamylamine, tyramine, n-methyl tyramine, synephrine, methyl-synephrine, theophylline, theobromine, theacrine, N,N-dimethyl phenethylamine, 1,3-dimethylbutylamine, oxilofrine, 1,5-dimethylhexylamine, N,alpha-diethylphenylethylamine, liberine, methylliberine, methyl caffeine, and pharmaceutically acceptable salts, esters, or amides thereof. In some aspects, the effective amounts of hexylamine or a salt thereof and of the stimulant are pharmaceutically effective amounts.

In another aspects, the nootropic composition comprises an effective amount of hexylamine or a salt thereof and an additional nootropic ingredient selected from the group consisting of: 5-HTP (5-hydroxytryptophan); carnitine or a salt, ester, or amide suitable for human ingestion thereof; acetyl-L-carnitine or a salt, ester, or amide suitable for human ingestion thereof; propionyl-L-carnitine or a salt, ester, or amide suitable for human ingestion thereof; alpha lipoic acid; alpha-GPC; aniracetam; piracetam; phenylpiracetam; apoaequorin; artichoke; ashwagandha; astaxanthin; *Bacopa monnieri*; cat's claw; catuaba, cannabidiol (CBD); *Celastris paniculatus*; centrophenoxine: citicoline; *Clitoria ternatea*; coluracetam; *Convolvulus pluricaulis*; ubiquinone (for example, Coenzyme Qio), creatine or a salt, ester, or amide suitable for human ingestion thereof; choline or a salt, ester, or amide suitable for human ingestion thereof; docosahexaenoic acid (DHA); dimethylethanolamine (DMAE);

forskolin; *Ginkgo biloba*; ginseng; gotu kola; guarana; kanna; kava kava; kratom, L-glutamine or a salt, ester, or amide suitable for human ingestion thereof; L-phenylalanine or a salt, ester, or amide suitable for human ingestion thereof, L-theanine or a salt, ester, or amide suitable for human ingestion thereof, L-tryptophan or a salt, ester, or amide suitable for human ingestion thereof, lecithin or a salt, ester, or amide suitable for human ingestion thereof, lemon balm; lion's mane mushroom; magnolia; medium chain triglycerides; reduced nicotinamide adenine dinucleotide (NADH); nefiracetam; nicotine; arecoline; noopept; oat-straw; oxiracetam; passion flower; phenibut; phosphatidylcholine; phosphatidylserine; picamilon; pine bark extract; pramiracetam; pyrroloquinoline quinone (PQQ); pterostilbene; resveratrol; rosemary; *Rhodiola rosea*; S-adenosyl methionine (SAMe); schizandrol-A; St. John's wort; sulbutiamine; taurine or a salt, ester, or amide suitable for human ingestion thereof, turmeric; L-tyrosine a salt, ester, or amide suitable for human ingestion thereof; N-acetyl-L-tyrosine a salt, ester, or amide suitable for human ingestion thereof; uridine; valerian; vinpocetine; thiamine or a salt, ester, or amide a salt, ester, or amide suitable for human ingestion thereof; niacin or a salt, ester, or amide suitable for human ingestion thereof, pantothenic acid or a salt, ester, or amide suitable for human ingestion thereof; vitamin B6 or a salt, ester, or amide suitable for human ingestion thereof, vitamin B8 or a salt, ester, or amide suitable for human ingestion thereof; vitamin B9 or a salt, ester, or amide suitable for human ingestion thereof; vitamin B12 or a salt, ester, or amide suitable for human ingestion thereof; and yerba mate. Where plants are listed above, all forms of the plants that are usable in formulating a supplement or pharmaceutical formulation, such as, powder, extracts, infusions, oils, etc. of the plant, are contemplated. The nootropic composition is more effective than the use of the additional nootropic ingredient alone. Accordingly, the nootropic composition may comprise less amount of the additional nootropic ingredient than the amount of the additional nootropic ingredient needed to have a positive nootropic effect. In some aspects, the effective amount of hexylamine or a salt thereof is a pharmaceutically effective amount.

As shown in Example 8, coadministration of hexylamine with a stimulant can prevent or reduce the side effects of the stimulant on the nervous system. Thus, the disclosure also relates to the use of hexylamine to prevent side effects of caffeine ingestion, for example, caffeine-induced jitters (feelings of extreme nervousness usually accompanied by trembling of the extremities) or a caffeine crash (feeling of drowsiness and lack of energy that develops hours after caffeine intake). The method comprises coadministering to the human subject an effective amount of caffeine and an effective amount of hexylamine or a salt thereof. In some aspects, the disclosure also relates to a composition for enhancing memory and/or increasing central nervous system activity comprising an effective amount of hexylamine or a salt thereof and an effective amount of caffeine. The effective amount of hexylamine or a salt thereof provides between about 5 mg and about 5000 mg hexylamine per day, for example, between 50 mg and 1000 mg, between 75 mg and 750 mg, between 100 mg and 750 mg, about 100 mg, about 250 mg, about 500 mg, about 600 mg, or about 750 mg. The effective amount of caffeine is between 50 mg and 600 mg, for example, between 50 mg and 500 mg, between 100 mg and 400 mg, between 100 mg and 300 mg, about 50 mg, about 100 mg, about 150 mg, about 300 mg, about 400 mg, about 500 mg, or about 600 mg.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1: Production of a Palatable Hexylamine Compound

In some aspects, salts of hexylamine are prepared by mixing liquid hexylamine into the desired acid. In other aspects, salts of hexylamine are prepared by mixing hexylamine and an acid in an appropriate solvent, such as ethanol. The salt is then separated from the solution by either recrystallization, evaporation of the solvent, or other similar methods of collecting the salt product Hexylamine succinate (structure shown in Formula II) was effectively synthesized by pouring an equimolar amount of hexylamine into succinic acid powder while continuously stirring in an ice bath so that the temperature of the salt solution would be over 131° C. Over the course of one week of storage, the succinate was surprisingly found to be non-hygroscopic and gain less than 1% water in the atmosphere.

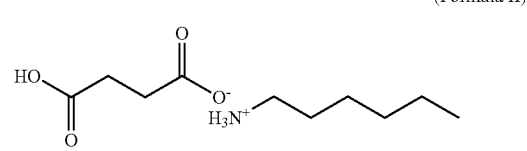

(Formula II)

Example 2: Comparison of Shelf Life for Hexylamine Succinate and Hexylamine Tartrate Hexylamine succinate and hexylamine tartrate were left exposed for a period of a month. As can be seen on the picture, hexylamine succinate (top beaker) remained a fine powder and gained little moisture. On the other hand, hexylamine tartrate (bottom beaker) absorbed moisture from the atmosphere and suffered from extensive caking.

Example 3: Human Tolerance of Hexylamine Succinate

A male human subject (38 years old, 250 lbs) was administered a single 100 mg hexylamine succinate, and his tolerance to the salt was record. The daily dose was increased increased daily to determine the highest daily dose that could be tolerance by the subject. At a daily dose of 800 mg and higher, the subject reported side effects such as feelings of discomfort.

Example 4: Effect of Hexylamine Supplementation on Human Subjects

Five human subjects were given 100-600 mg hexylamine succinate each day over a period of a month or four weeks (see Table 1). The subjects all experienced increased mental acuity, reduced appetite, increased body temperature, increased sweating, improved mood, reduction of fatigue, notable reduction in appetite, increase in athletic performance, increase in endurance, increase in strength, increase in blood pressure by an average of 8 mm for systolic blood pressure and 2 mm for diastolic blood pressure, increase in heart rate, improved memory recollection.

TABLE 1

| Subject | Notes | Age (Years) | Weight (lbs.) | Dose administered |
|---|---|---|---|---|
| 1 | Male, Trained | 38 | 240 | 200 mg |
| 2 | Male, Elite trained | 26 | 260 | 400 mg |
| 3 | Female, Untrained, Mild Depression, PTSD | 32 | 150 | 100 mg |
| 4 | Male, Trained | 55 | 210 | 200 mg |
| 5 | Male, Overweight | 35 | 220 | 500 mg |

Over the course of the treatment period, two of the subjects who ingested hexylamine daily experienced a weight loss of 3 pounds without making any changes to their diet or exercise regimen. With the administration of 600 mg hexylamine succinate (equaling 276 mg of hexylamine base), the subjects' body temperature would rise by about 0.5° C.

Hexylamine was generally well-tolerated. None of the subjects experienced any of the toxic side effects described for too much exposure hexylamine, which include, burning sensation, abdominal pain, shock, or collapse. However, the effectiveness would diminish with doses less than 100 mg.

Example 5: Citrate Salts of Hexylamine

The salt form of hexylamine plays a major role in the stability and possession of activity (or lack thereof) of hexylamine. Some salt forms like the fumarate possessed little to no activity, accompanied by issues with their stability, solubility, dissolution rate and hygroscopicity. Other forms, like the nitrate salt, were liquid at standard room temperature and pressure, which made those forms unsuitable for most formulations. In fact, the nitrate salt is very irritating on contact with the skin or mouth. Applicant developed a novel, non-conventional hexylamine salt, tri-hexylamine citrate ($C_{24}H_{53}N_3O_7$ or $3(C_6H_{16}N^+) \cdot C_6H_5O_7^{3-}$, calculated molar mass of 495.69 g/mol), which possesses all the desirable properties for a safe and effective hexylamine supplement: fast dissolution rate, superior solubility, non-toxic, and stable at standard temperature and pressure.

Tri-hexylamine citrate has the following molecular structure (Formula III):

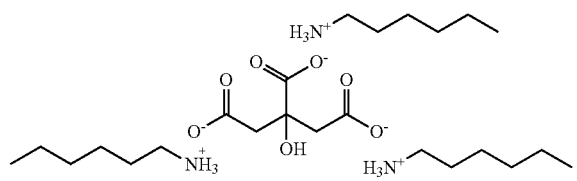

Whereas the calculated theoretical percentage of citric acid in the salt would be ~39%, the certificate of analyzed for the synthesized hexylamine salt reported a citric acid was 43%. This difference could be attributed to a variety of environmental factors, for example, moisture in the tested sample or overabundance of one of the reactants. Direct combination of citric acid and hexylamine does not form tri-hexylamine citrate. Instead, the process forms mono-hexylamine citrate, as evidenced by the salt having triple the density than hexylamine. Whereas tri-hexylamine citrate floats on water, mono-hexylamine citrate sinks to the bottom. Mono-hexylamine citrate also has a much slower dissolution rate in water when compared with tri-hexylamine citrate. At standard temperature and pressure, mono-hexylamine citrate has the consistency of a paste, which makes it unsuitable for formulation or for further reactions. The consistency also indicates mono-hexylamine citrate is highly hygroscopic.

To efficiently produce tri-hexylamine citrate, hexylamine should be slowly added to a saturated solution of citric acid in acetone. At room temperature, the saturated solution of citric acid in acetone is prepared by adding 20 g citric acid to 1000 ml acetone. The amount of citric acid dissolvable in acetone is higher with higher temperatures. However, acetone evaporates at around 80° C. and is a fire and health hazard, so the preparation of the saturated solution of citric acid in acetone should not use acetone heated to a temperature higher than 70° C., preferably no higher than 40° C.

Also at room temperature, triple the molar amount of hexylamine was added drop by drop added to the saturated solution of citric acid in acetone while the saturated solution of citric acid in acetone is continually stirred. During the addition of hexylamine to the saturated solution of citric acid in acetone, white solid mass will form. Upon completion of addition of the hexylamine, the mixture was left to stir for another 15 minutes. Then the mixture was filtered and dried under air current. The final weight of the white solid mass formed from reacting 20 g citric acid with 31.5 g hexylamine was 51.2 grams.

Example 6: Safety and Efficacy of Tri-Hexylamine Citrate

Twelve healthy human subjects were recruited for a study to determine the safety of tri-hexylamine citrate supplementation and whether tri-hexylamine citrate supplementation improves mood and cognitive function (as measured by a psychomotor vigilance test, Iowa trail making test, and digit symbol substitution test). The lasted two days.

Each morning, the blood pressure of the subjects was measured, and the subjects completed a questionnaire to describe their mood before the subjects were orally administered either placebo dose (dextrose capsule) or 1000 mg tri-hexylamine citrate (containing about 600 mg hexylamine). If the subject received the placebo dose on day one, then the subject received tri-hexylamine citrate on day two, and vice versa. The administration of placebo or tri-hexylamine citrate was random, and both the subject and the person administering the test were blinded. The mood assessment involves the subjects self scoring on a scale of 1-10, with ten being the greatest, regarding whether the extent they feel sleepy, groggy, energetic, attentive, focused, tense, alert, nervous, happy, and sad.

The blood pressure of the subjects was measured 15 minutes after administration of the placebo dose or tri-hexylamine citrate, and the subjects completed a questionnaire to describe their mood a second time. Afterwards, the subjects completed a psychomotor vigilance test via the sleep-2-Peak mobile application (Brunet et al., "Validation of sleep-2-Peak. A smartphone application that can detect fatigue-related changes in reaction times during sleep deprivation," *Behav Res*, 2017, 49:1460-1469), Iowa trail making test, and the digit symbol substitution test (DSST) to assess their cognitive function. After the completion of the tests, the blood pressure of the subjects was measured were measured a third time, and the subjects completed a questionnaire to describe their mood a third time. At 50 minutes after administration, the blood pressure of the subjects was measured were measured a fourth time, and the subjects completed a questionnaire to describe their mood a fourth time.

None of the subjects experienced any discomfort or any serious side effect from hexylamine supplementation. Results from self-mood assessment test did not show any statistically significant results. The blood pressure of the subjects was largely unaffected by tri-hexylamine citrate supplementation. As a group, no significant difference in systolic blood pressure, diastolic pressure, or heart rate was observed. The systolic blood pressure of four of the subjects were significantly different as a result of tri-hexylamine; however, only three of these subjects exhibited a statistically significant decrease in systolic blood pressure. This result goes against conventional wisdom that possible neuroactive amines will cause increase in blood pressure as well the results in Example 4, which showed moderate increase in blood pressure from administration of hexylamine succinate. Thus hexylamine supplementation appears to be safe, but it may not be a suitable treatment for hypotension.

Statistically significant results were obtained from the cognitive function tests. The average reaction times as measured by the sleep-2-Peak mobile application was significantly reduced as a result of tri-hexylamine citrate (−70.1 msec or 18%, p=0.0015). This reduction is greater than the reduction of reaction time from a study where subjects were given an energy drink containing 300 mg caffeine energy drink (Antonio et al., "The Effects of an Energy Drink on Psychomotor Vigilance in Trained Individuals," *J. Funct. Morphol. Kinesiol.* 2019, 4, 47), which reported that the energy drink only reduced reaction times by less than 5% (278.8±47.7 msec for placebo vs 265.0±44.7 msec for energy drink).

The Iowa trail making test assesses visual attention and task switching. In map A, the subject is to draw lines to connect circled numbers in a numerical sequence (1-2-3- . . . ) as rapidly in possible. In map B, the subject is to draw lines to connect circled numbers and letters in an alternating numeric and alphabetic sequence (1-A-2-B- . . . ) as rapidly as possible. Accordingly, map A assesses cognitive processing speed, while map B asses executive function. If the subject makes an error, it was immediately pointed it out and the subject was allowed correct it. Accordingly, errors affect the score only in that the correction of errors is included in the completion time for the task. Whereas hexylamine reduced the average time the subjects needed for completing map A and map B, only the reduction for the completion of map B was statistically significant (−12.5 sec, p=0.0020). Thus, hexylamine administration improves executive function.

The DSST is a cognitive function test designed to understand human associative learning. The subjects receive a single sheet of paper that requires them to match symbols to numbers according to a key located on the top of the page. The subjects copy the symbol into spaces below a row of numbers. The number of correct symbols within the allowed time, usually 90 to 120 seconds, constitutes the score. A good performance on the DSST requires intact motor speed, attention, and visuoperceptual functions, including scanning and basic manual dexterity. Thus, the DSST is sensitive to impairments and improvement in processing speed, executive functioning, and working memory. Administration of tri-hexylamine citrate to subjects improved to average DSST score by 3.2 points, which is a 6% improvement (p=0.0020). Accordingly, hexylamine administration improves associative learning and the ability to complete tasks requiring intact motor speed, attention, and visuoperceptual functions, including scanning and basic manual dexterity.

Example 7: Effect of Tri-Hexylamine Citrate on Physical Performance

Four human subjects ingested 1000 mg tri-hexylamine citrate 30 minutes before performing their regular exercise. Compared with their performance without taking any supplement or medication, all subjects reported they were able to perform greater number of repetitions on knee extensions and the bench press. On the treadmill, all subject reported longer time to exhaustion. In addition, all subjects reported feeling more focused and energetic. During and after exercise, they also reported feeling a reduced sense of fatigue.

Example 8: Effect of Administration of Tri-Hexylamine Citrate and Caffeine

Five subjects who are caffeine users ingested 1 g tri-hexylamine citrate along with 300 mg caffeine in a capsule. None of the subjects reported any jittery sensation (feelings of extreme nervousness usually accompanied by trembling of the extremities) or a caffeine crash (feeling of drowsiness and lack of energy that develops hours after caffeine intake). They subjects experience at leas tone of these side effects when they ingested 300 mg caffeine alone. Thus, contrary to the previous expectation that co-administration of hexylamine would increase side effects of CNS activity promoters, co-administration of hexylamine with caffeine reduced the side effects of caffeine.

Example 9: Exemplary Compositions Comprising Hexylamine

I. Pre-Workout Powder Comprising Hexylamine to Increase Athletic Performance (Per Dose):
   10 g citrulline malate
   2 g citrulline nitrate
   2 g betaine
   1 g betaine nitrate
   2.6 g beta alanine
   1 g beta alanine nitrate
   2 g proline
   1 g proline nitrate
   1 g black tea extract
   368 mg caffeine
   1000 mg hexylamine (in the form of trihexylamine citrate)
   300 mg ferulic acid
   200 mg theanine
   1 mg 5-MTHF
   10 mg elemental zinc
II. Fat Loss Aid Supplement (Per Dose)
   300 mg green tea extract
   1000 mg hexylamine (in the form of tri-hexylamine citrate)
   60 mg synephrine
   200 mg 5-HT
   1000 mg acetyl-L-carnitine
III. Nootropic Formulation for Boosting Cognitive Function (Per Dose)
   1000 mg hexylamine (in the form of tri-hexylamine citrate)

100 mg caffeine 100 mg
100 mg theanine 100 mg
200 mg alpha-GPC
10 mg vitamin B6
1 mg vitamin B12

IV. Topical Gel for Assisting in Topical Fat Loss
10 g hydrogel base
100 mg hexylamine (in the form of tri-hexylamine citrate)
50 mg caffeine
1 mg capsaicin

We claim:

1. A method of producing tri-hexylamine citrate, the method comprising:
   dissolving an amount of citric acid in a solvent to produce a saturated solution of citric acid, wherein the solvent does not chemically react to citric acid or hexylamine and the citric acid and hexylamine are both soluble in the solvent; and
   adding an amount of hexylamine to the saturated solution of citric acid to produce a mixture containing a precipitate, wherein the molar ratio of the amount of the hexylamine to the amount of citric acid is 3:1, wherein the amount of hexylamine is added drop by drop.

2. The method of claim 1, wherein the saturated solution of citric acid is continually stirred while the amount of hexylamine is being added.

3. The method of claim 1, wherein the solvent is acetone.

4. The method of claim 3, wherein the amount of citric acid is dissolved in acetone at room temperature.

5. The method of claim 3, wherein the amount of citric acid is dissolved in acetone at a temperature of less than 70° C.

6. The method of claim 1 further comprising:
   stirring the mixture containing the precipitate for at least fifteen minutes;
   filtering out the precipitate from the mixture; and
   drying the precipitate to collect tri-hexylamine citrate.

* * * * *